(12) United States Patent
Nakano

(10) Patent No.: US 6,999,556 B2
(45) Date of Patent: Feb. 14, 2006

(54) RADIATION THERAPY TREATMENT PLANNING MACHINE

(75) Inventor: Hirokazu Nakano, Yokohama (JP)

(73) Assignee: Nakano System Company, Shizuoka-ken (JP)

( * ) Notice: Subject to any disclaimer, the term of this patent is extended or adjusted under 35 U.S.C. 154(b) by 104 days.

(21) Appl. No.: 10/731,090

(22) Filed: Dec. 10, 2003

(65) Prior Publication Data

US 2004/0184578 A1    Sep. 23, 2004

(30) Foreign Application Priority Data

Mar. 19, 2003 (JP) .............................. 2003-074910

(51) Int. Cl.
*A61N 5/10* (2006.01)
*G21K 1/04* (2006.01)

(52) U.S. Cl. ......................................... 378/65; 378/152

(58) Field of Classification Search .................... 378/2, 378/65, 147, 150, 151, 152, 64
See application file for complete search history.

(56) References Cited

U.S. PATENT DOCUMENTS

| 5,818,902 | A | * | 10/1998 | Yu ................................ | 378/65 |
| 6,052,430 | A | * | 4/2000 | Siochi et al. .................. | 378/65 |
| 6,687,330 | B1 | * | 2/2004 | Hernandez-Guerra ........ | 378/65 |
| 6,879,659 | B1 | * | 4/2005 | Alber .......................... | 378/65 |
| 6,907,105 | B1 | * | 6/2005 | Otto ............................. | 378/65 |

FOREIGN PATENT DOCUMENTS

| JP | 1-214343 | 8/1989 |
| JP | 2564251 | 9/1996 |

OTHER PUBLICATIONS

Rolf Staehelin, entitled *"Intensity Modulated Radiation Therapy—A Breakthrough in Oncology"*, Marketing Europe, Varian Medical Systems, Inc., Business Briefing: Global Healthcare 2003.

Martijn Engelsman, et al., entitled *"Impact of Simple Tissue Inhomogeneity Correction Algorithms on Conformal Radiotherapy of Lung Tumours"*, Radiother. Oncol. Chapter IV 60, 229-309 (2001).

Kazuhiro Takahashi, et al., entitled *"Work in Progress: Treatment Planning System for Conformation Radiotherapy"*, Radiology, vol. 147, No. 2, pp. 567-573.

(Continued)

*Primary Examiner*—Allen C. Ho
(74) *Attorney, Agent, or Firm*—Wenderoth, Lind & Ponack, L.L.P.

(57) ABSTRACT

In an RTP machine, for a series of leaf positions which are generated by a Multileaf-Collimator-Position-Calculation-Unit, a speed limit is established by a Motion-Speed-Limit-Establishing-Unit. Further, a Motion-Display-Unit indicates the area where motion speed exceeds the established speed and/or a Leaf-Position-Correction-Unit controls the area in order to be equal to or less than the established speed limit. Furthermore, a Motion-Acceleration-Calculating-Unit calculates motion acceleration of the multileaf collimator, and the Motion-Display-Unit indicates the area where the calculated motion acceleration exceeds the established limit and/or the Leaf-Position-Correction-Unit controls the area in order to be equal to or less than the established acceleration limit. An interruption of irradiation due to a multileaf collimator positioning error is prevented while the treatment is being conducted by the multileaf collimator motion limit control in radiation therapy such as conformal therapy or others which the multileaf collimator moves in during irradiation.

25 Claims, 19 Drawing Sheets

OTHER PUBLICATIONS

Toni Neicu, et al., entitled "*Synchronized Moving Aperture Radiation Therapy (Smart); Average Tumour Trajectory for Lung Patients*", Institute of Physics Publishing, Phys. Med. Biol. 48 (2003) pp. 587-598.

Tony Xu, et al., entitled "*Reshapable Physical Modulator for Intensity Modulated Radiation Therapy*", Med. Phys. 29 (10), Oct. 2002, pp. 2222-2229:.

Lei Xing, et al., entitled "*Iterative Methods for Inverse Treatment Planning*", Phys. Med. Biol. 41 (1996), pp. 2107-2123.

Paul S. Cho, et al., entitled "*Hardward-Sensitive Optimization for Intensity Modulated Radiotherapy*", Phys. Med. Biol. 45 (2000), pp. 429-440.

Srijit Kamath, et al., entitled "*Leaf Sequencing Algorithms for Segmented Multileaf Collimation*", Pys. Med. Biol 48 (2003), pp. 307-324.

P. Xia, et al., entitled "*Physical Characteristics of a Miniature Multileaf Collimator*", Med. Phys. 26 (1), Jan. 1999, pp. 65-70.

A. Boyer et al., entitled "*Theoretical Considerations of Monitor Unit Calculations for Intensity Modulated Beam Treatment Planning*", Med. Phys. 26 (2), Feb. 1999, pp. 187-195.

Jeff M. Michalski, M.D. et al., entitled "*Three-Dimensional Conformal Radiation Therapy (3DCRT) for Prostate Cancer*", Jul. 6, 1996, pp. 1-10.

Chandra Burman, PhD, entitled "*Prostate IMRT: Promises and Problems*", Memorial Sloan-Kettering Cancer Center, New York, NY 10021. Aug. 11, 2003.

Jessica Chen, entitled "*Minimising IMRT Treatment Time by Optimal Configuration of Multileafcollimators*", Department of Operational Research, University of Auckland, New Zealand. Nov. 2002.

C.C. J. Yang et al., entitled "*Intensity Modulated Radiation Therapy: High Definition Radiationtherapy*", pp. 55-62. Summer 2001.

D. Tronc, et al., entitled "*Radiotherapy Process Integration Using a Compact Photon Source Together with Fluence Control and Patient Imaging*", General Electric Medical System, BP 334, 78 533 Buc Cedex, France. Nov. 14, 1994.

Jack Van Dyk, et al., entitled "*Tomotherapy: A "Revolution" in Radiation Therapy*", pp. 1-16. Mar./Apr. 2002.

James A. Purdy et al., "Advances in Radiation Oncology Physics". Medical Physics Monograph No. 19. pp. 307-354. Jul. 15-20, 1990.

Radhe Mohan et al., "A Comprehensive Three-Dimensional Radiation Treatment Planning System". Int. J. Radiation Oncology Biol. Phys., vol. 15, pp. 481-495. 1988.

A.R. Hounsell et al., "Computer-assisted generation of multi-leaf collimator settings for conformation therapy", The British Journal of Radiology, vol. 65, pp. 321-326. 1992.

\* cited by examiner

RADIATION THERAPY TREATMENT PLANNING MACHINE

BACKGROUND OF THE INVENTION

1. Field of the Invention

The present invention relates to a radiation therapy treatment planning (hereafter referred to as RTP) machine to plan for cancer treatment with radiation therapy. The present invention more specifically relates to an RTP machine preferably used for treatment planning in cases where radiation is applied while changing the radiation field by a multileaf collimator.

2. Description of the Related Art

Radiation therapy is one method of cancer treatment utilizing radiation. In radiation therapy it is preferable that high radiation dosage is irradiated on the target, and radiation dosage as low as possible is irradiated on organs other than the target. Therefore, a treatment plan is necessary for applying radiation therapy. A machine to deliver this treatment plan is referred to as an RTP machine.

FIG. 6 is a perspective view showing the constitution of a radiation therapy treatment machine called a linear accelerator (hereafter referred to as linac). The linac includes a gantry 61, a collimator 62, a rotation shaft 64 for the gantry 61, a couch 65, and a rotation shaft 66 for the couch 65. Gantry 61 incorporates a beam source in its head, and rotates about rotation shaft 64 in the directions indicated by arrow A in the drawing. Collimator 62 is connected with the head of gantry 61, and rotates in the directions indicated by arrow B in the drawing. Collimator 62 incorporates a multileaf collimator, and the radiation ray from the radiation source inside gantry 61 is masked to any field shape, and then, irradiates toward couch 65. Couch 65 is utilized to support the patient, and rotates about couch rotation shaft 66 in the directions of C in the drawing. Couch rotation shaft 66 coincides with a vertical line in a state where collimator 62 is facing downward. In general, the gantry angle 0 degrees is defined in the linac when collimator 62 is facing directly downward, and the angle increases clockwise. FIG. 6 shows where the gantry angle is 0 degrees. In general, a linac can rotate from 180 degrees to 180 degrees passing through 0 degrees. When the radiation ray irradiates the target, it is necessary to irradiate from a direction that avoids critical organs such as the eyeball and the spinal cord by changing the gantry angle, the collimator angle, and the couch angle.

FIG. 7 is a perspective view showing the construction of a multileaf collimator (hereafter referred to as MLC). In this drawing, the MLC includes upper jaws 71, lower jaws 72, and leaves 73. Upper jaws 71 move to open and close in directions indicated by arrows L1 and L2. Lower jaws 72 include a number of leaves 73, and move to open and close in directions W1 and W2. The individual leaves 73 move independently to alter the radiation field shape. The intersection between gantry rotation shaft 64 and a perpendicular line extending down from the beam source is referred to as an isocenter. A plane which has this isocenter as a center is in line with the gantry rotation shaft 64, and crosses at right angles with a perpendicular line extending down from the gantry head is referred to as an isocenter plane. An isocenter is often used as a reference point for dosage calculation, and a beam usually irradiates such that the center of the target would be at the isocenter. The field shape of radiation usually refers to this shape on the isocenter plane.

FIG. 8 shows a sectional view representing the radiation field on the isocenter plane formed by the MLC. The drawing indicates the upper jaws 71, the lower jaws 72, the location of the pointed radiation beam source 85 of the linac, the isocenter plane 86, the center axis of the radiation beam 84, and the radiation field 87. The beam emitted from beam source 85 forms radiation field 87 on isocenter plane 86, blocking the ray by using upper jaws 71 and leaves 73 of lower jaws 72.

The radiation therapy technique, where the isocenter is positioned inside the patient's body and irradiates with a fixed gantry, is referred to as the SAD technique. The radiation therapy technique, where the isocenter is positioned on the patient skin, is referred to as the SAD technique. The radiation therapy technique, which irradiates the target while the gantry is rotating, is referred to as rotational therapy. The isocenter is usually positioned inside the patient's body with the rotational therapy. The radiation therapy technique, where the radiation field matches the target shape with the fixed gantry, is referred to as irregular field radiation therapy. In addition, the radiation therapy technique, which irradiates with fixed beams while the gantry angle switches, is referred to as irregular field multi-beam radiation therapy. The radiation therapy technique, where the radiation field formed by the MLC matches the target shape by adjusting the leaf positions while the gantry is rotating to concentrate radiation on the target, is referred to as conformal therapy.

FIG. 9 shows how the radiation field shape of conformal therapy changes during the gantry rotation. Reference number 91 indicates the radiation field shape when the gantry angle is 216 degrees, reference number 92 indicates the radiation field shape when the gantry angle is 288 degrees, reference number 93 indicates the radiation field shape when the gantry angle is 0 degrees, reference number 94 indicates the radiation field shape when the gantry angle is 72 degrees, and reference number 95 indicates the radiation field shape when the gantry angle is 144 degrees. Conformal therapy is a method to rotate the linac beam source around the target, and simultaneously, to adjust the positions of the MLC installed at the beam source of the radiation ray so as to form the radiation field to correspond with the shape of the affected part. Actual examples to generate MLC positions from a target shape are disclosed in the Japanese Patent Application Publication H01-214343, Japanese Patent Application Publication H08-131566, and others.

The following section briefly describes how to generate the MLC positions. Computer Tomography, CT, images are examined to diagnose the location and the shape of the cancer. The CT images are used to confirm the location of the affected part in three dimensions by examining images usually at intervals of 1 cm around the affected part of the patient. Then, the contours of the affected part namely the cancer are extracted from this group of the CT images. For conformal therapy, the MLC leaf positions are usually calculated from contours which are extracted from the CT images projected in two dimensions seen from the gantry angle with a certain width of margin processing. In other words, while the gantry is rotating and irradiating, the shape of the cancer at the gantry angle is changing so that the leaves are being moved to fit the changes so as to alter the radiation field to dose radiation to the cancer effectively and to avoid irradiating to normal tissue as much as possible. This calculation for the MLC leaf positions is conducted by a Multileaf-Collimator-Position-Calculation-Unit.

IMRT is one type of irregular field multi-beam radiation therapy which has been utilized recently. IMRT is an abbreviation of Intensity Modulated Radiation Therapy, and is one radiation therapy technique used to modulate the beam intensity to irradiate unevenly in order to distribute optimal dosage. Actual examples of this beam intensity modulated radiation therapy are the step-and-shoot method and the sliding-window method.

FIG. 10 is a drawing showing the radiation field shapes by the MLC of the step-and-shoot method. In this drawing, reference numbers 101a, 101b, 101c, and 101d are segments of the radiation field shapes when the gantry angle is 216 degrees, reference number 102 indicates the radiation field shape when the gantry angle is 288 degrees, reference number 103 indicates the radiation field shape when the gantry angle is 0 degrees, reference number 104 indicates the radiation field shape when the gantry angle is 72 degrees, and reference number 105 indicates the radiation field shape when the gantry angle is 144 degrees. The step-and-shoot method is conducted as one irregular field multi-beam radiation therapy. The radiation field shapes at each angle consist of multiple radiation fields where the MLC forms discretionary shapes referred to as segments. In this example, four segments are used for each radiation angle, and each segment accumulates radiation dosage by turning the beam on and off. In the example in FIG. 10, where the gantry angle is 216 degrees, irradiation is provided with four patterns as segment 101a, 101b, 101c, and 101d. At other gantry angles, irradiation is similarly provided with different shapes of radiation fields at multiple times, and each dosage is accumulated in order to distribute optimal dosage.

FIG. 11 is a drawing showing the MLC radiation field shape of the sliding window method. In this drawing, reference number 111 indicates the radiation field shape when the gantry angle is 216 degrees, reference number 112 indicates the radiation field shape when the gantry angle is 288 degrees, reference number 113 indicates the radiation field shape when the gantry angle is 0 degrees, reference number 114 indicates the radiation field shape when the gantry angle is 72 degrees, and reference number 115 indicates the radiation field shape when the gantry angle is 144 degrees.

The sliding window method is conducted as one type of irregular field multi-beam radiation therapy, and irradiates with beams, the intensity of which are modulated by the MLC which continuously moves while irradiating. Reference numbers 111, 112, 113, 114, and 115 show how the MLC leaf positions change. In contrast to the step-and-shoot method, the beam is not turned on or off during one irradiation. This irradiation is conducted from each irradiation direction (gantry angle). This method is to distribute the optimal dosage by accumulating each series of irradiation at each angle with moving and controlling the MLC.

An RTP machine is constituted of hardware equipment such as a computer main unit, a keyboard, a monitor, a scanner, a printer, and software to control them. It plans how to operate the linac based on methods such as the aforementioned different types of radiation therapy, and creates data to control the gantry angle, the collimator angle, the MLC positions, the couch angle, the radiation dosage, and others. The created data is input into a linac, which operates according to the data, and a radiation therapy is provided as planned by the RTP machine.

In conformal therapy and IMRT sliding window method, the leaf positions change during the irradiation. An MLC is constituted of a number of metal leaves, and the individual leaves are driven by motors to control their positions. Therefore, when the leaves move, the leaf motion speed is limited by the motor revolution speed limit, and the leaf motion acceleration is also limited by the leaf momentum and the motor torque. When MLC leaf motion speed or acceleration exceeds the tolerance and then a leaf positioning error has occurred due to going over the acceptable range, the linac usually detects an error and deactivates itself. Though there are some types of linacs which are capable of resuming after the MLC positioning has been completed, in general the operator has to reset the treatment parameters according to the deactivated status. In either case, since radiation output of a linac cannot rise quickly, there would be an error with the treatment plan. In case of a pneumatic drive or a hydraulic drive to control the MLC, there would still be a speed and torque limit as with the motor drive.

SUMMARY OF THE INVENTION

The objective of the present invention is to devise an RTP machine which is capable of generating data reflected by the MLC leaf limits of the motion speed and acceleration.

The present invention provides a radiation therapy treatment planning machine for use with a multileaf collimator. In one aspect of the present invention, the machine comprises: a Multileaf-Collimator-Position-Calculation-Unit operable to generate multileaf collimator leaf positions as a time series; a Motion-Speed-Calculating-Unit operable to calculate leaf motion speed based on the generated time series leaf positions; a Motion-Speed-Limit-Establishing-Unit operable to establish a motion speed limit of the leaves; and a Motion-Display-Unit operable to indicate leaf motion information and to indicate the motion information of an area where the calculated motion speed exceeds the established motion speed limit.

In one embodiment of the above aspect, the Motion-Speed-Limit-Establishing-Unit comprises a Motion-Speed-Limit-Inputting-Unit operable to input a motion speed limit of the leaves as the established motion speed limit. Further the machine can comprise: a Motion-Acceleration-Calculating-Unit operable to calculate leaf motion acceleration based on the time series leaf positions generated by the Multileaf-Collimator-Position-Calculation-Unit; and a Motion-Acceleration-Limit-Inputting-Unit operable to input a motion acceleration limit of the leaves, wherein the Motion-Display-Unit is further operable to indicate the motion information of an area where the calculated motion acceleration exceeds the inputted acceleration limit.

In another embodiment of the above aspect, the Motion-Speed-Limit-Establishing-Unit comprises a Motion-Speed-Limit-Setting-Unit operable to set a predetermined motion speed limit of the leaves as the established motion speed limit. Further the machine can comprise: a Motion-Acceleration-Calculating-Unit operable to calculate leaf motion acceleration based on the time series leaf positions generated by the Multileaf-Collimator-Position-Calculation-Unit; and a Motion-Acceleration-Limit-Setting-Unit operable to set a predetermined motion acceleration limit of the leaves, wherein the Motion-Display-Unit is further operable to indicate the motion information of an area where the calculated motion acceleration exceeds the predetermined set acceleration limit.

In another embodiment of the above aspect, the machine can further comprise: a Motion-Acceleration-Calculating-Unit operable to calculate leaf motion acceleration based on the time series leaf positions generated by the Multileaf-Collimator-Position-Calculation-Unit, wherein the Motion-Display-Unit is further operable to indicate the motion information of an area where the calculated motion acceleration exceeds a motion acceleration limit.

In another aspect of the present invention, the machine comprises: a Multileaf-Collimator-Position-Calculation- Unit operable to generate multileaf collimator leaf positions as a time series; a Motion-Speed-Calculating-Unit operable to calculate leaf motion speed based on the generated time series leaf positions; a Motion-Speed-Limit-Establishing-Unit operable to establish a motion speed limit of the leaves; and a Leaf-Position-Correction-Unit operable to correct the leaf positions of an area, where the calculated motion speed exceeds the inputted motion speed limit, in order for the leaf motion speed to be equal to or less than the established motion speed limit.

In one embodiment of the above aspect, the Motion-Speed-Limit-Establishing-Unit can comprises a Motion-Speed-Limit-Inputting-Unit operable to input a motion speed limit of the leaves as the established motion speed limit. Further the machine can comprise a Motion-Acceleration-Calculating-Unit operable to calculate leaf motion acceleration based on the leaf positions corrected by the Leaf-Position-Correction-Unit; and a Motion-Acceleration-Limit-Inputting-Unit operable to input a motion acceleration limit of the leaves, wherein the Leaf-Position-Correction-Unit is further operable to correct the leaf positions of an area, where the calculated motion acceleration exceeds the inputted acceleration limit, in order for the leaf motion acceleration to be equal to or less than the inputted acceleration limit. In any event, leaf positions can be corrected toward a direction to widen the radiation field shape when the Leaf-Position-Correction-Unit corrects the leaf positions of an area where the calculated motion speed exceeds the inputted motion speed limit in order for the leaf motion speed to be equal to or less than the inputted motion speed limit. Alternatively, leaf positions can be corrected toward a direction to narrow the radiation field shape when the Leaf-Position-Correction-Unit corrects the leaf positions of an area where the calculated motion speed exceeds the inputted motion speed limit in order for the leaf motion speed to be equal to or less than the inputted motion speed limit.

In another embodiment of the above aspect, the Motion-Speed-Limit-Establishing-Unit can comprise a Motion-Speed-Limit-Setting-Unit operable to set a predetermined motion speed limit of the leaves as the established motion speed limit. Further the machine can comprise: a Motion-Acceleration-Calculating-Unit operable to calculate leaf motion acceleration based on the leaf positions corrected by the Leaf-Position-Correction-Unit; and a Motion-Acceleration-Limit-Setting-Unit operable to set a predetermined motion acceleration limit of the leaves, wherein the Leaf-Position-Correction-Unit is further operable to correct the leaf positions of an area, where the calculated motion acceleration exceeds the predetermined set acceleration limit, in order for the leaf motion acceleration to be equal to or less than the predetermined set acceleration limit. In any event, leaf positions can be corrected toward a direction to widen the radiation field shape when the Leaf-Position-Correction-Unit corrects the leaf positions of an area where the calculated motion speed exceeds the predetermined set motion speed limit in order for the leaf motion speed to be equal to or less than the predetermined set motion speed limit. Alternatively, leaf positions can be corrected toward a direction to narrow the radiation field shape when the Leaf-Position-Correction-Unit corrects the leaf positions of an area where the calculated motion speed exceeds the predetermined set motion speed limit in order for the leaf motion speed to be equal to or less than the predetermined set motion speed limit.

In another aspect of the present invention, the machine comprises: a Multileaf-Collimator-Position-Calculation-Unit operable to generate multileaf collimator leaf positions as a time series; a Motion-Acceleration-Calculating-Unit operable to calculate leaf motion acceleration based on the generated time series leaf positions; Motion-Acceleration-Limit-Establishing-Unit operable to establish a motion acceleration limit of the leaves; and a Motion-Display-Unit operable to indicate leaf motion information of an area where the calculated motion acceleration exceeds the established acceleration limit. Still further, the Motion-Acceleration-Limit-Establishing-Unit can comprise a Motion-Acceleration-Limit-Inputting-Unit operable to input a motion acceleration limit of the leaves as the established motion acceleration limit. Alternatively, the Motion-Acceleration-Limit-Establishing-Unit can comprise a Motion-Acceleration-Limit-Setting-Unit operable to set a predetermined motion acceleration limit of the leaves as the established motion acceleration limit.

In another aspect of the present invention, the machine comprises: a Multileaf-Collimator-Position-Calculation-Unit operable to generate multileaf collimator leaf positions as a time series; a Motion-Acceleration-Calculating-Unit operable to calculate leaf motion acceleration based on the generated time series leaf positions; Motion-Acceleration-Limit-Establishing-Unit to establish a motion acceleration limit of the leaves; and a Leaf-Position-Correction-Unit operable to correct the leaf positions of an area, where the calculated motion acceleration exceeds the established motion acceleration limit, in order for the leaf motion acceleration to be equal to or less than the established motion acceleration limit. Still further, the Motion-Acceleration-Limit-Establishing-Unit can comprise a Motion-Acceleration-Limit-Inputting-Unit operable to input a motion acceleration limit of the leaves as the established motion acceleration limit. Alternatively, the Motion-Acceleration-Limit-Establishing-Unit can comprise a Motion-Acceleration-Limit-Setting-Unit operable to set a predetermined motion acceleration limit of the leaves as the established motion acceleration limit.

The RTP machine, according to the present invention, is capable of having different functions to display and correct the leaf positions when either the speed or the acceleration exceeds the limit. In the present invention, when the leaf positions are corrected in order for the leaf motion to be equal to or less than the limit, there are two ways to correct the leaf positions: firstly toward a direction to widen the radiation field shape (to open the leaves) and secondly toward a direction to narrow the radiation field shape (to close the leaves). Which method is adopted depends on the case.

The Multileaf-Collimator-Position-Calculation-Unit, the Motion-Speed-Calculating-Unit, the Motion-Speed-Limit-Inputting-Unit, the Motion-Speed-Limit-Setting-Unit, the Motion-Display-Unit, the Leaf-Position-Correction-Unit, the Motion-Acceleration-Calculating-Unit, the Motion-Acceleration-Limit-Inputting-Unit and the Motion-Acceleration-Limit-Setting-Unit are all functions which have been programmed into the software in the present invention.

The Multileaf-Collimator-Position-Calculation-Unit is a function of the software to generate MLC leaf positions conventional publicly-known RTP machines.

The Motion-Speed(Acceleration)-Calculating-Unit is a function of the software which calculates leaf motion speed (or acceleration) based on the time series leaf positions generated by the Multileaf-Collimator-Position-Calculation-Unit.

The Motion-Speed(Acceleration)-Limit-Inputting-Unit is a function of the software which shows an input screen, lets an operator input the leaf speed (or acceleration) limit and sets the input value.

The Motion-Speed(Acceleration)-Limit-Setting-Unit is a function of the software which reads the speed (or acceleration) limit from the software itself—or from a parameter list—and sets the value.

The Motion-Display-Unit is a function of the software to display at least the area where the leaf motion speed (or acceleration) calculated by the Motion-Speed(Acceleration)-Calculating-Unit exceeds the limit, e.g., it displays the area on the monitor screen or on the print-out.

The Leaf-Position-Correction-Unit is a function of the software to correct the leaf positions of the area where the calculated motion speed (or acceleration) exceeds the limit, in order for the leaf motion speed (or acceleration) to be equal to or less than the limit.

According to the present invention, the RTP machine restricts the MLC leaf motion speed and acceleration within the limit or displays the area where the motion exceeds the limit and warns the operator. Accordingly, when the linac actually treats a patient, it is possible to prevent a dosage distribution different to that the treatment plan because of the MLC leaf positioning error and it is possible to prevent the linac from stopping as a result of detecting the error and de-activating itself.

DETAILED DESCRIPTION OF THE PREFERRED EMBODIMENTS

The following embodiment is described as an example of conformal therapy. Conformal therapy is a method to continuously irradiate while a gantry rotates and an MLC changes. For conformal therapy, MLC leaf positions are usually calculated from projected contours which are extracted from the CT images in two dimensions seen from the gantry angle of the rotation with a certain width of margin processing. While the gantry is rotating and irradiating, the shape of the cancer (target) at the gantry angle changes continuously, the leaves are moved to fit the changes. For a conformal therapy plan, the leaf positions are usually generated with each two degrees of the gantry angle and the leaf position's resolution is generally 1 mm. For conformal therapy, rotation of the gantry means elapse of time, namely, changing angle means passing time. The time series leaf positions are generated by the Multileaf-Collimator-Position-Calculation-Unit, and this Multileaf-Collimator-Position-Calculation-Unit is conventionally and publicly known in.

The RTP machine of the present embodiment includes a Motion-Speed-Calculating-Unit, a Motion-Speed-Limit-Inputting-Unit, a Motion-Display-Unit, a Leaf-Position-Correction-Unit, a Motion-Acceleration-Calculating-Unit and a Motion-Acceleration-Limit-Inputting-Unit in addition to a Multileaf-Collimator-Position-Calculation-Unit. The leaf speed limit of the linac is input at the Motion-Speed-Limit-Inputting-Unit. The leaf acceleration limit of the linac is input at the Motion-Acceleration-Limit-Inputting-Unit.

Figure 1:
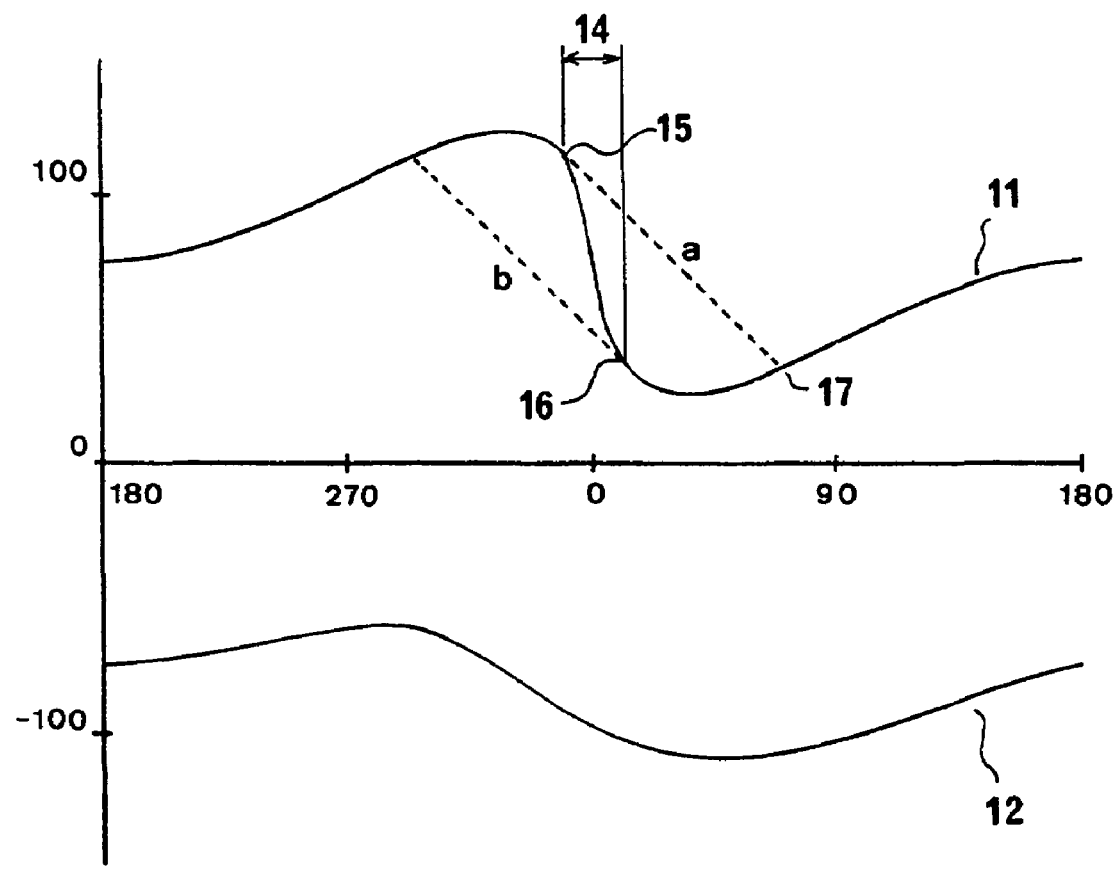
FIG. 1 is a trace of a pair of the leaves from the gantry rotation start angle to the end angle in conformal therapy according to the present invention.

FIG. 1 shows a trace of a pair of the leaves from the gantry rotation start angle to the end angle in conformal therapy. In the drawing, reference number 11 indicates a curve of a leaf's trace in conformal therapy, and reference number 12 indicates a curve of an opposite of the leaf's trace in conformal therapy. An MLC consists of a number of leaf pairs; a leaf pair consists of two leaves. Curve 11 and curve 12 represent the traces of each leaf of the leaf pair. The leaf speed is the difference of the leaf positions (gradient of curve 11 and curve 12) between a certain time interval (in each two degrees), and the leaf acceleration is the difference of the speeds between a certain interval (in each two degrees). The Motion-Speed-Calculating-Unit calculates motion speed of the individual leaves based on the time series leaf positions (corresponding to curve 11 and curve 12) generated by the Multileaf-Collimator-Position-Calculation-Unit. The Motion-Acceleration-Calculating-Unit calculates the motion acceleration of the leaves based on the time series leaf positions (corresponding to the curve 11 and curve 12) generated by the Multileaf-Collimator-Position-Calculation-Unit.

The following section describes the Leaf-Position-Correction-Unit. The Leaf-Position-Correction-Unit compares the leaf motion speed (or acceleration) which is calculated by the Motion-Speed(Acceleration)-Calculating-Unit with the preset limit, and when the leaf motion speed (or acceleration) exceeds the limit, the Leaf-Position-Correction-Unit controls the leaf positions in order to be equal to or less than the limit.

In FIG. 1, reference (a) is a dotted line of a case which opens the leaf, reference (b) is a dotted line of a case which closes the leaf, reference number 14 is an area where the leaf speed exceeds the limit, reference number 15 is a start point of the area where the leaf speed exceeds the limit, reference number 16 is an end point of the area where the leaf speed exceeds the limit, and reference number 17 is an intersection of the dotted line (a) and curve 11. It is assumed that curve 11 and curve 12 have 2 degrees and 1 mm resolution. The drawing shows the clockwise gantry rotation from 180 degrees as the lowest point to 180 degrees passing through 0 degrees as the highest point. On curve 11, there is area 14 where the leaf speed exceeds the limit around 0 degrees. The dotted line (a) shows an example where the leaf position correction starts from start point 15 of area 14 toward the direction to open the leaf compared with the position before the correction, and the dotted line (b) shows an example where the correction starts from end point 16 of area 14 toward the direction to close the leaf In general, when there are no critical organs near the organ having cancer to be irradiated, the correction to close the leaf may cause insufficient dosage of irradiation, therefore the correction to open the leaf is preferable. When there is a critical organ near the cancer, the condition determines which correction would be more preferable, to open or to close.

Figure 2:
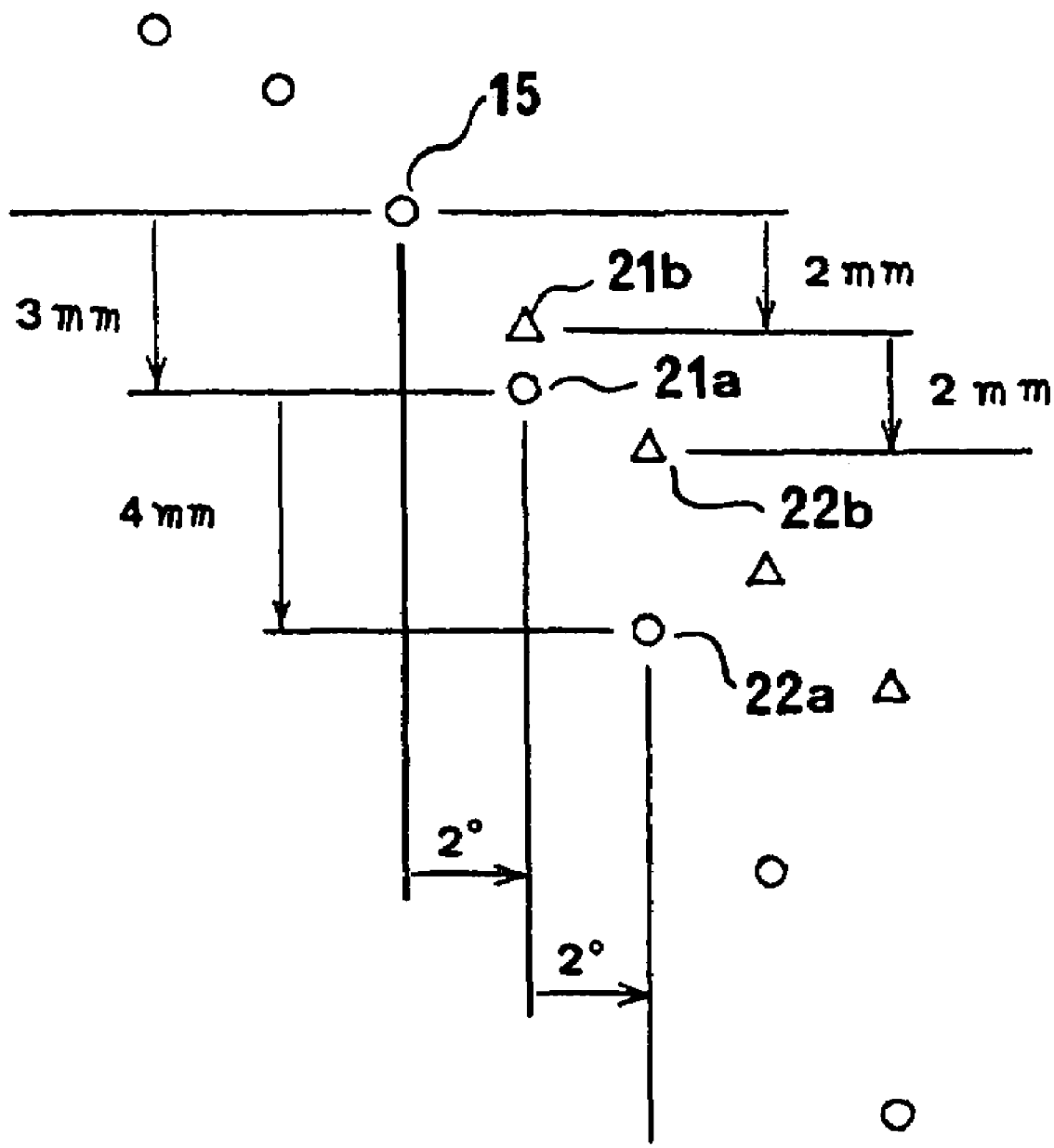
FIG. 2 is an enlarged view at start point 15 of area 14 in FIG. 1.
Figure 3:
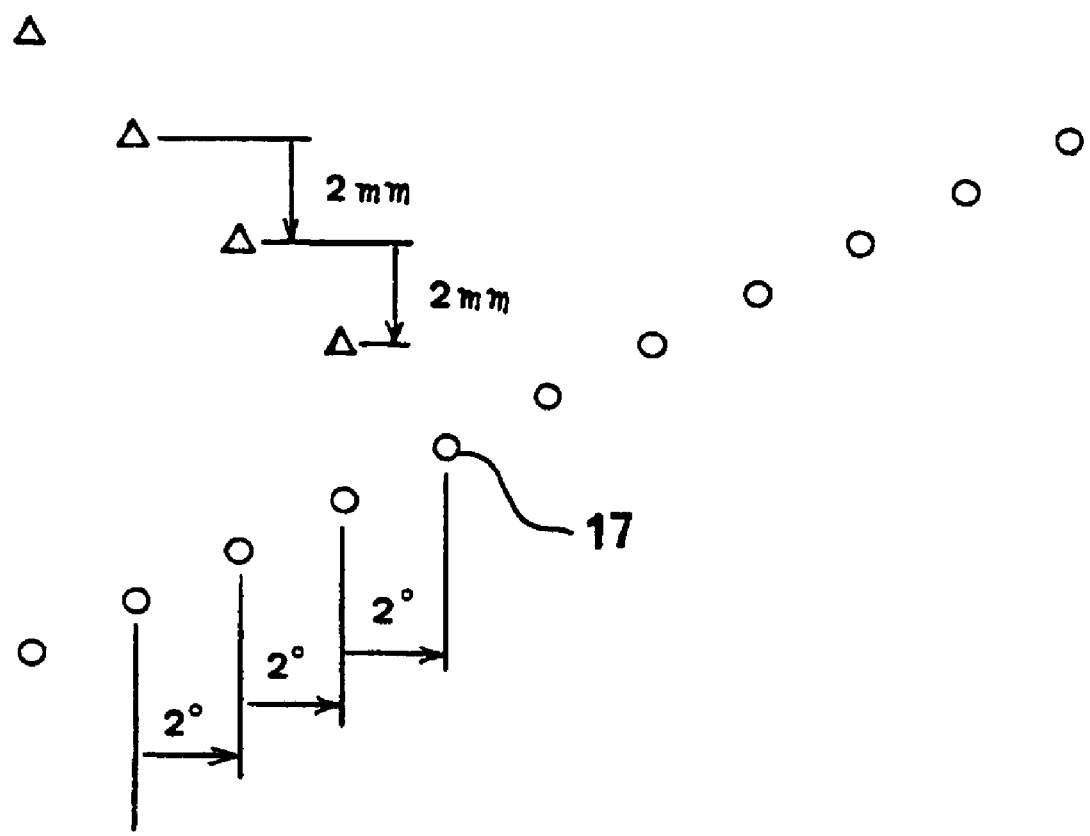
FIG. 3 is an enlarged view at intersection 17 in FIG. 1.

FIG. 2 is an enlarged view at start point 15 of area 14 in FIG. 1. In this drawing, reference number 21a indicates a point next to start point 15, reference number 21b indicates a point next to start point 15 after the correction, 22a is a point next to 21a, and 22b is a point next to 21b after the correction. The leaf motion speed limit is generally 2 to 9 mm per 2 degrees and the value depends on the linac. The present embodiment is an example where the leaf motion control uses 2 mm per 2 degrees as the leaf motion speed limit. Symbols □ in the drawing are leaf positions corresponding to the curve 11 in FIG. 1, and symbols Δ are leaf positions when the motion control is applied, and corresponds to the dotted line (a) in FIG. 1. The leaf motion distance from start point 15 to point 21a is 3 mm. This value exceeds the motion limit of 2 mm, and motion control is applied at point 21a. Wherein the motion distance from start point 15 is limited to 2 mm. Point 22a is compared with point 21b, and since the accumulated difference is 5 mm, this point is controlled in order for the difference to be equal to or less than 2 mm and moved to point 22b. This operation is sequentially applied to each point, thereby the dotted line (a) in FIG. 1 is eventually obtained.

Figure 4:
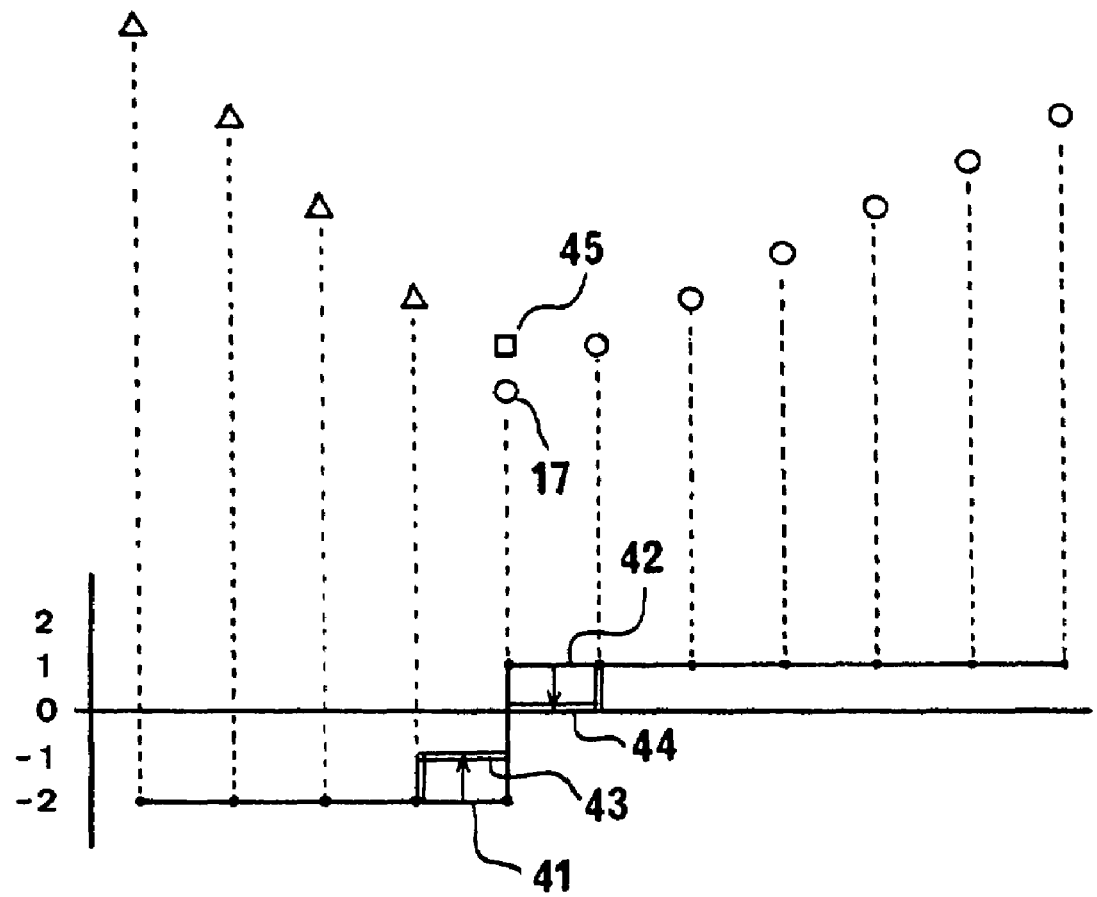
FIG. 4 is an example where the acceleration limit control is applied to intersection 17 in FIG. 1.

FIG. 4 is an example where the acceleration limit control is applied of intersection 17 in FIG. 1. In the drawing, reference number 41 indicates the speed from the preceding point at intersection 17, reference number 42 indicates the speed to the following point at intersection 17, reference number 43 indicates the speed at which the acceleration limit control is applied to the speed indicated at reference number 41, reference number 44 indicates the speed at which the acceleration limit control is applied to the speed indicated at reference number 42, and reference number 45 indicates the leaf position at which the acceleration limit control is applied to intersection 17. In the present embodiment, it is assumed that the acceleration limit is 2. Since the speed indicated at reference number 41 is −2, and the speed indicated at reference number 42 is 1, the acceleration at intersection 17 is the difference between them, 3. Since a leaf is usually made of metal and has considerable weight, the direction of motion cannot be changed quickly due to the inertia. The output of the driving motors have a torque limit in addition to a revolution speed limit, and the motion of the leaf at intersection 17 could be a cause of a positioning error.

The following section describes an acceleration limit control processing.

The Motion-Acceleration-Calculating-Unit calculates leaf motion acceleration based on the time series leaf positions which are generated by the Multileaf-Collimator-Position-Calculation-Unit (corresponding to curve 11 and curve 12) and corrected by the Leaf-Position-Correction-Unit (corresponding to the dotted line (a) or (b)). The Leaf-Position-Correction-Unit corrects the leaf positions when the leaf motion acceleration exceeds the limit. In this case, since the acceleration at intersection 17 exceeds the limit, the speed indicated at reference number 41 and the speed indicated at reference number 42 at intersection 17 are both corrected with the same value to decrease the difference between them. In the present embodiment, the speed indicated at reference number 41 is corrected to the speed indicated at reference number 43, and the speed indicated at reference number 42 is corrected to the speed indicated at reference number 44 by a factor of 1 for each. Based on the equation that speed×distance=position and to maintain the continuity of the positions, the summation of the corrected areas should be 0 (zero). In this case, the area from reference number 41 to reference number 43 and the area from reference number 42 to reference number 44 are equal with opposite direction, therefore they cancel each other out, and the summation of the areas becomes 0 (zero). As a result of the leaf position correction, the operation moves point 17 to point 45 and makes the acceleration at point 45 to a factor of 1 which is equal to or less than the acceleration limit. The described section is an operation to apply to a pair of leaves, the described operations are applied to other MLC leaves to calculate speed and acceleration and to correct leaf positions. While in the present embodiment, the motion speed (acceleration) limit is an input parameter by the operator, it is also possible to comprise a Motion-Speed(Acceleration)-Limit-Setting-Unit which provides the parameter as the linac own value (written in the parameter list) or to comprise a fixed parameter in the program.

The method to correct the leaf positions in the case of excessive speed or excessive acceleration in the present embodiment is simply an example, and it should be noted that different methods could be adopted.

The following section describes an example of IMRT sliding window method.

Figure 5:
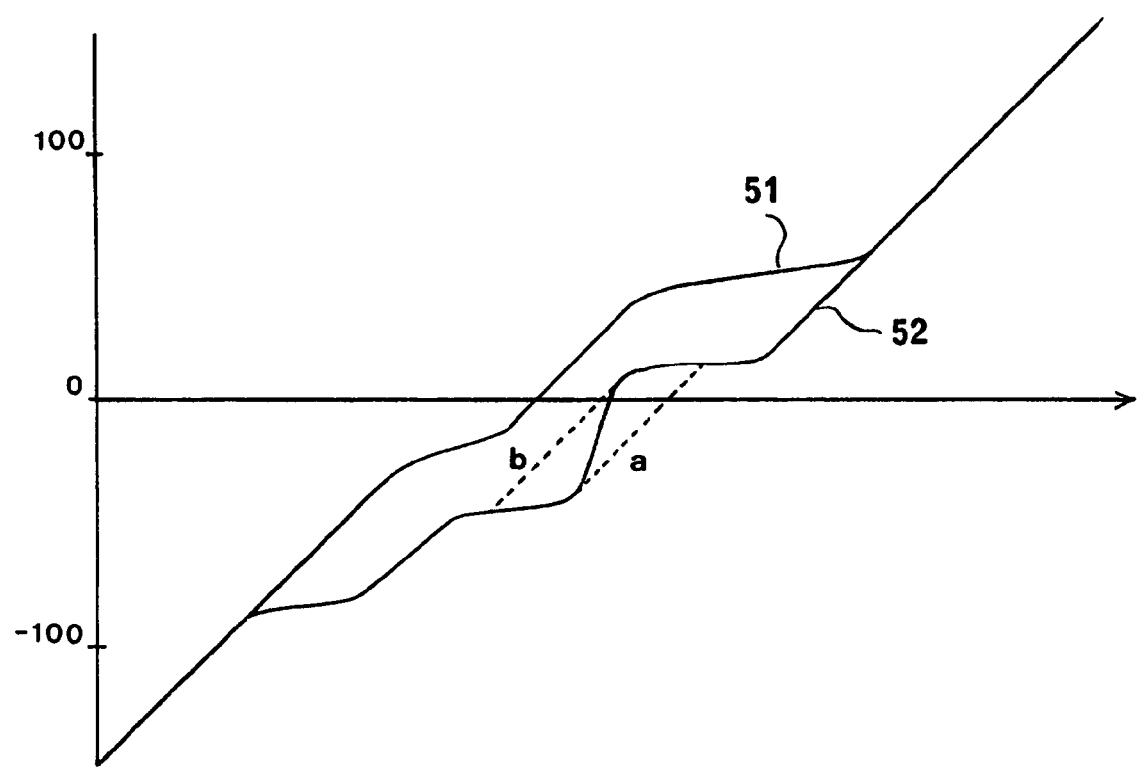
FIG. 5 is a trace of a pair of the leaves during radiation with IMRT sliding window method according to the present invention.
Figure 6:
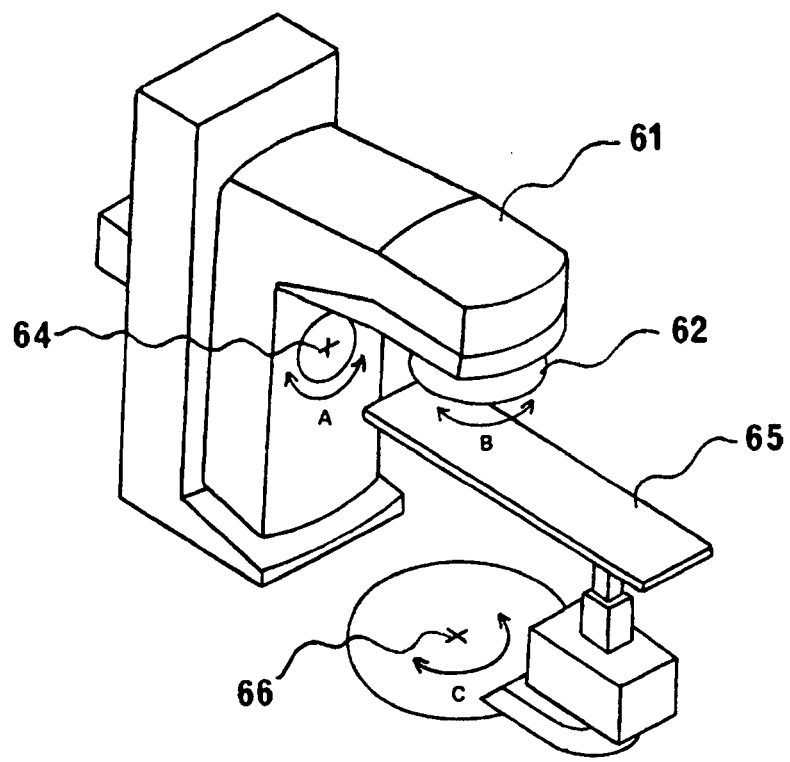
FIG. 6 is a perspective view of a linac.
Figure 7:
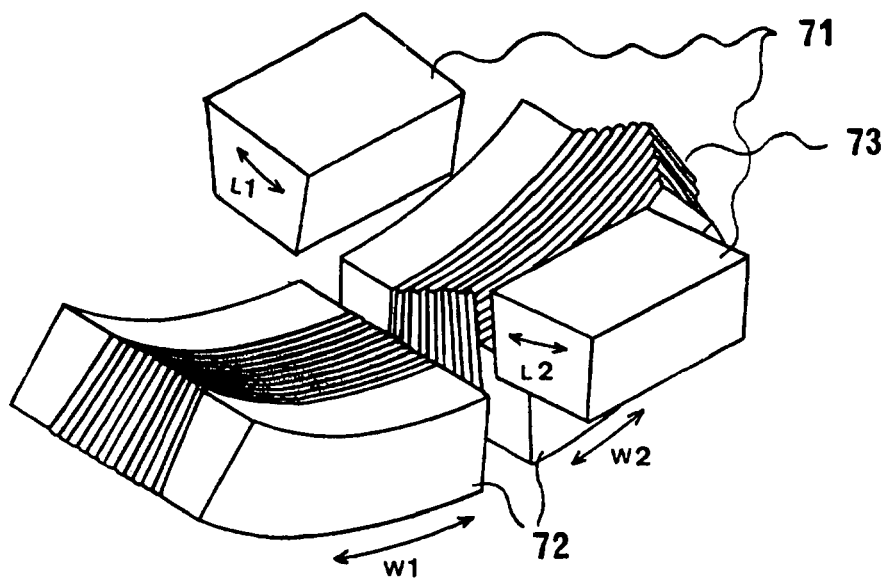
FIG. 7 is a perspective view of a multileaf collimator.
Figure 8:
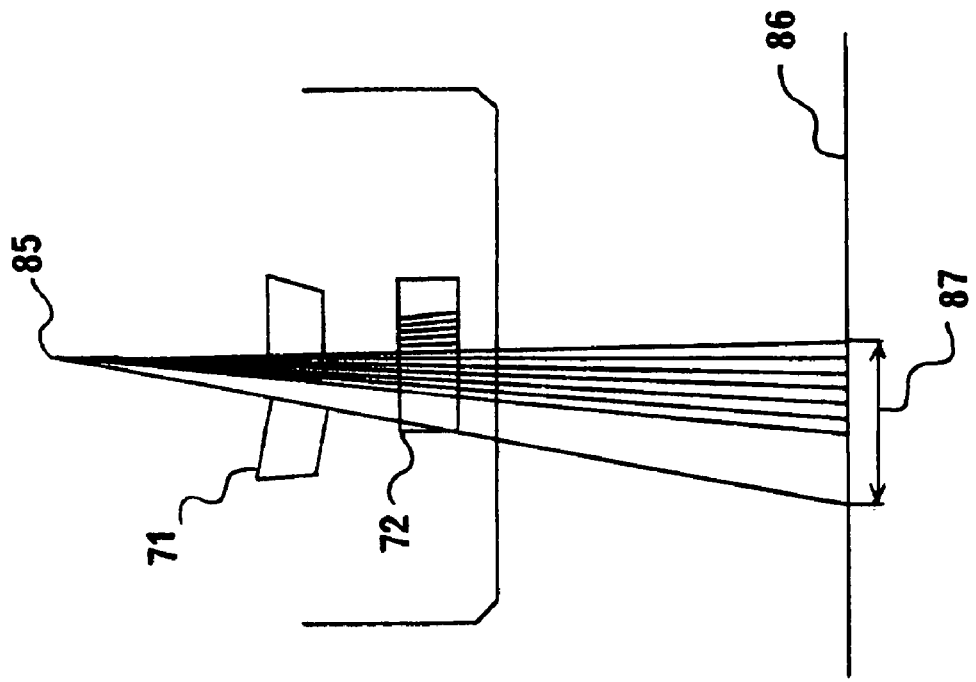
FIGS. 8A and B are sectional views representing the radiation field on the isocenter plane formed by the MLC.
Figure 8:
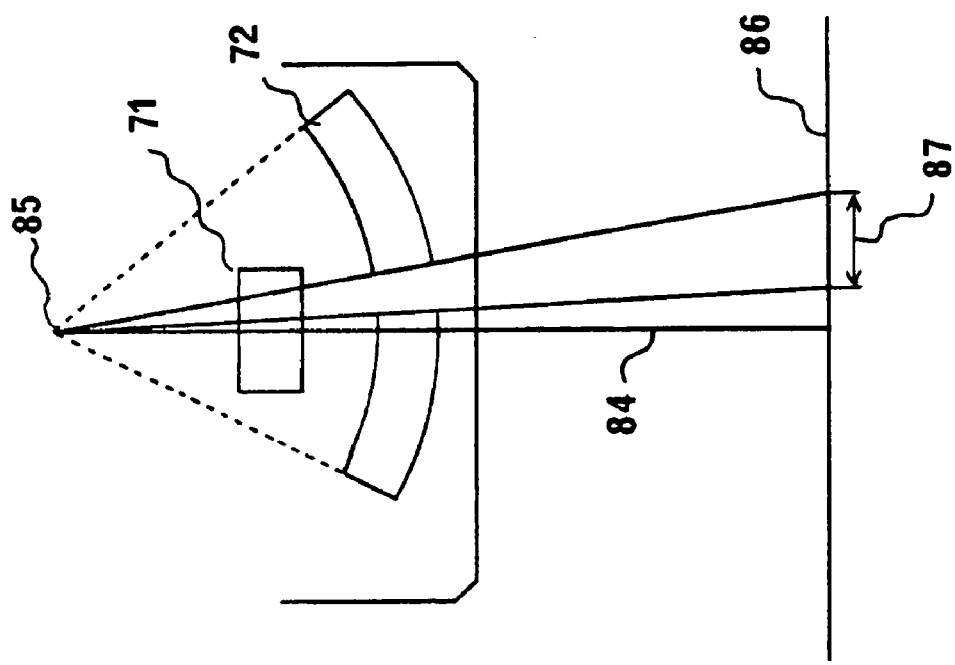
Figure 9:
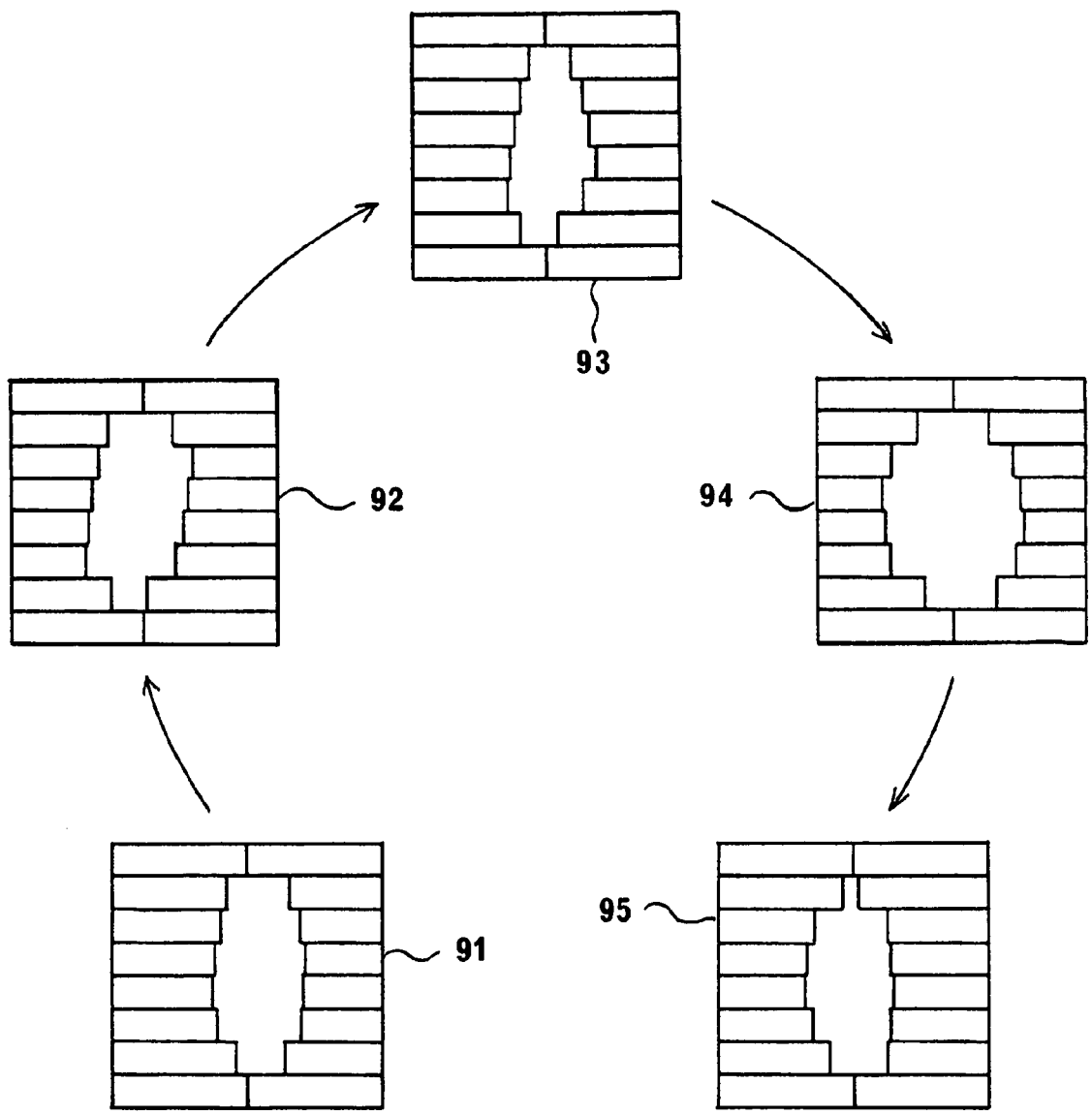
FIG. 9 illustrates how the radiation field shape of conformal therapy changes during the gantry rotation.
Figure 10:
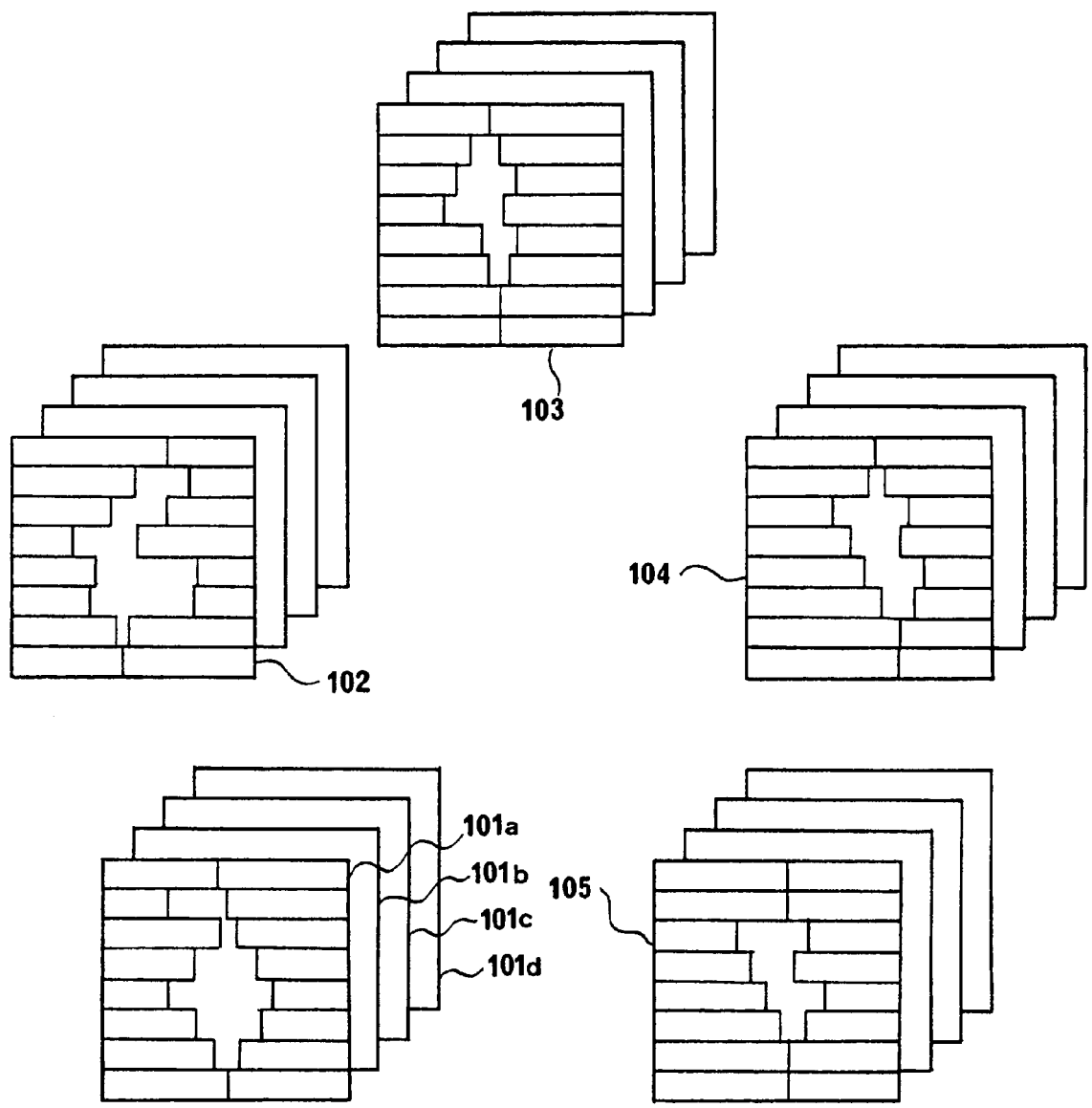
FIG. 10 illustrates the radiation field shapes by the MLC of the step-and-shoot method.
Figure 11:
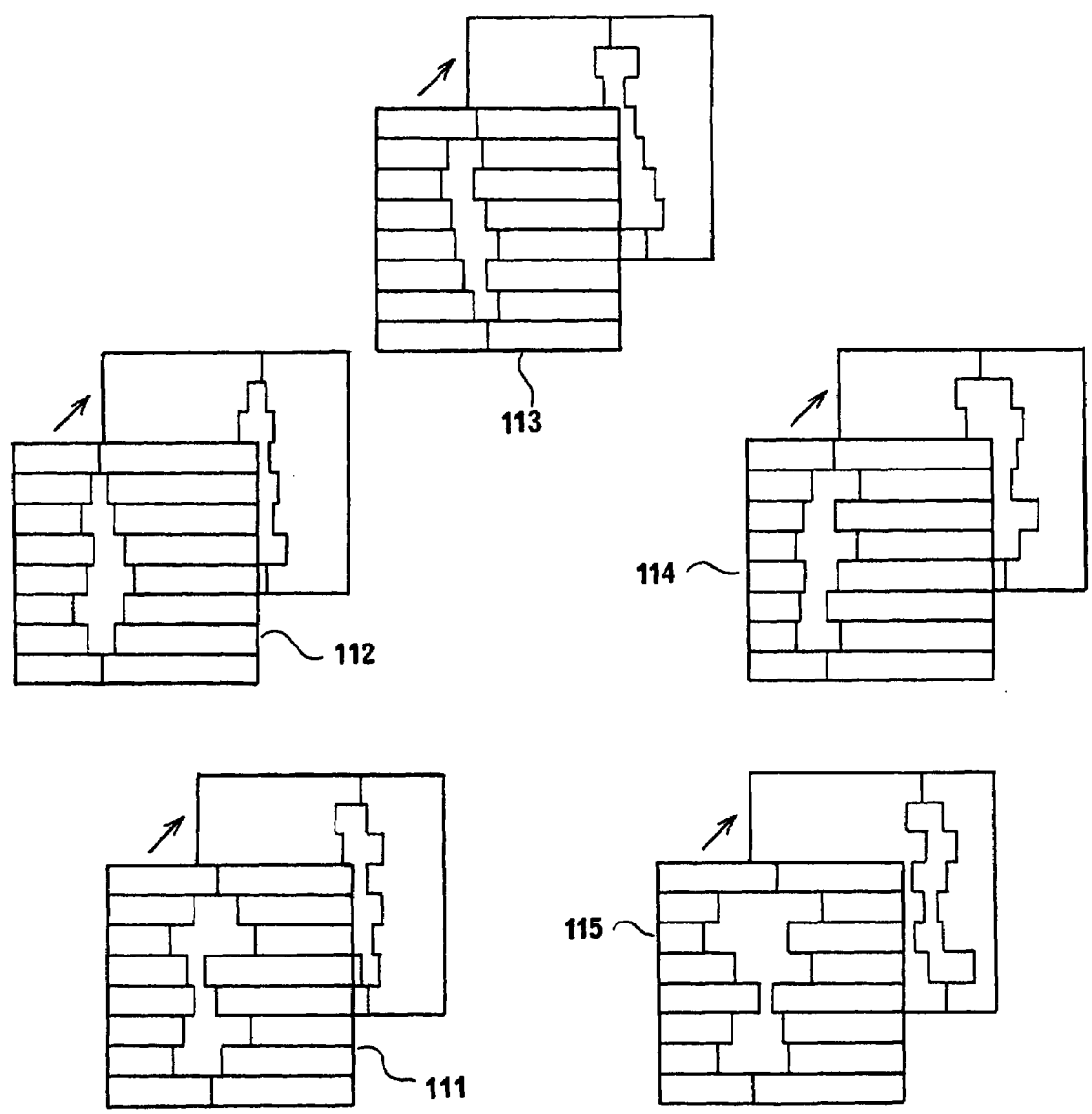
FIG. 11 illustrates the MLC radiation field shape of the sliding window method.
Figure 12:
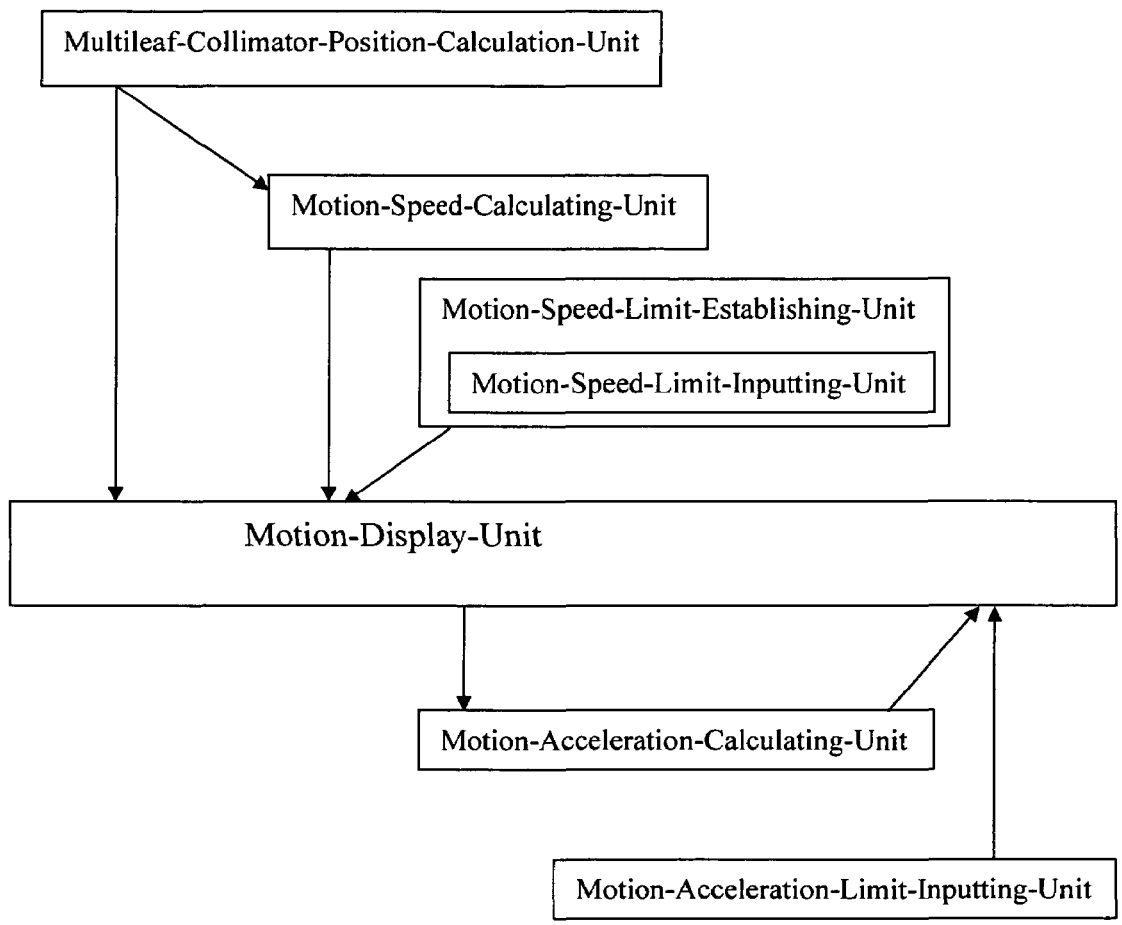
FIG. 12 is a block diagram showing a first aspect of the present invention.
Figure 13:
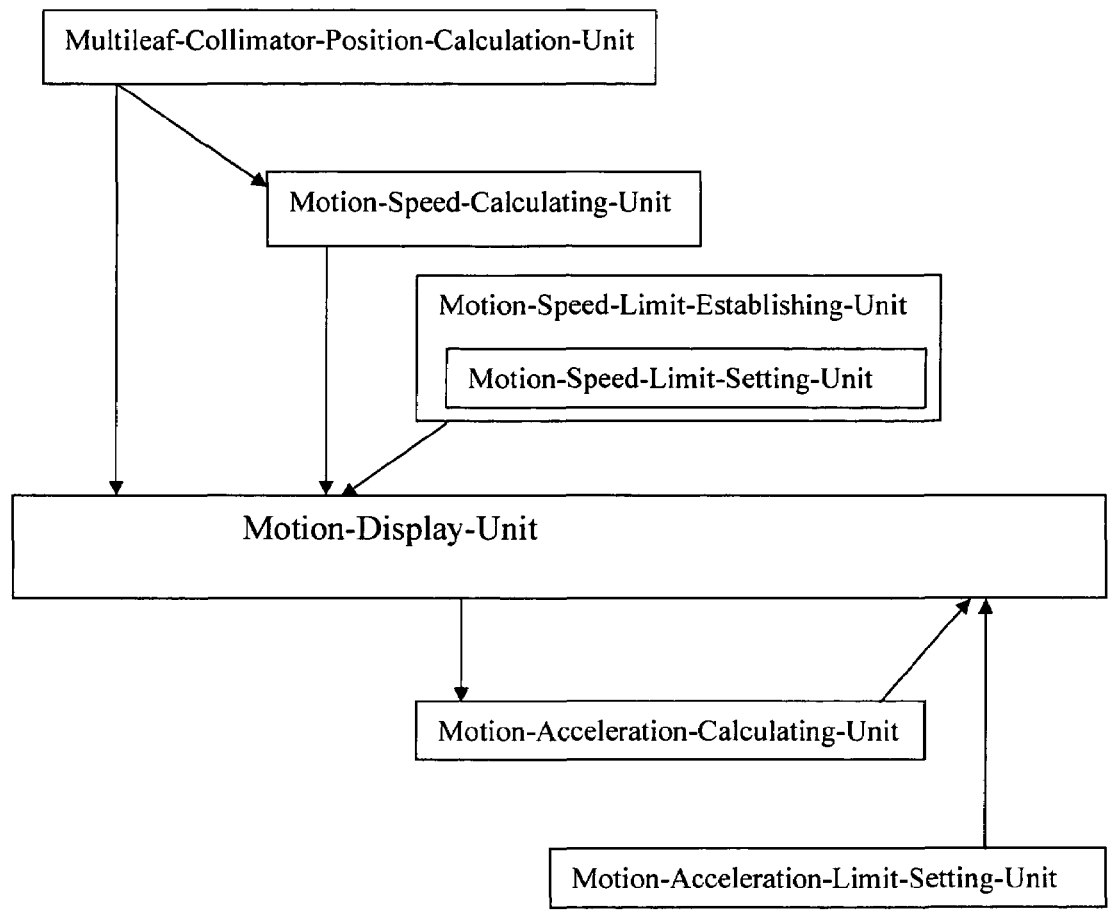
FIG. 13 is a block diagram showing a second aspect of the present invention.
Figure 14:
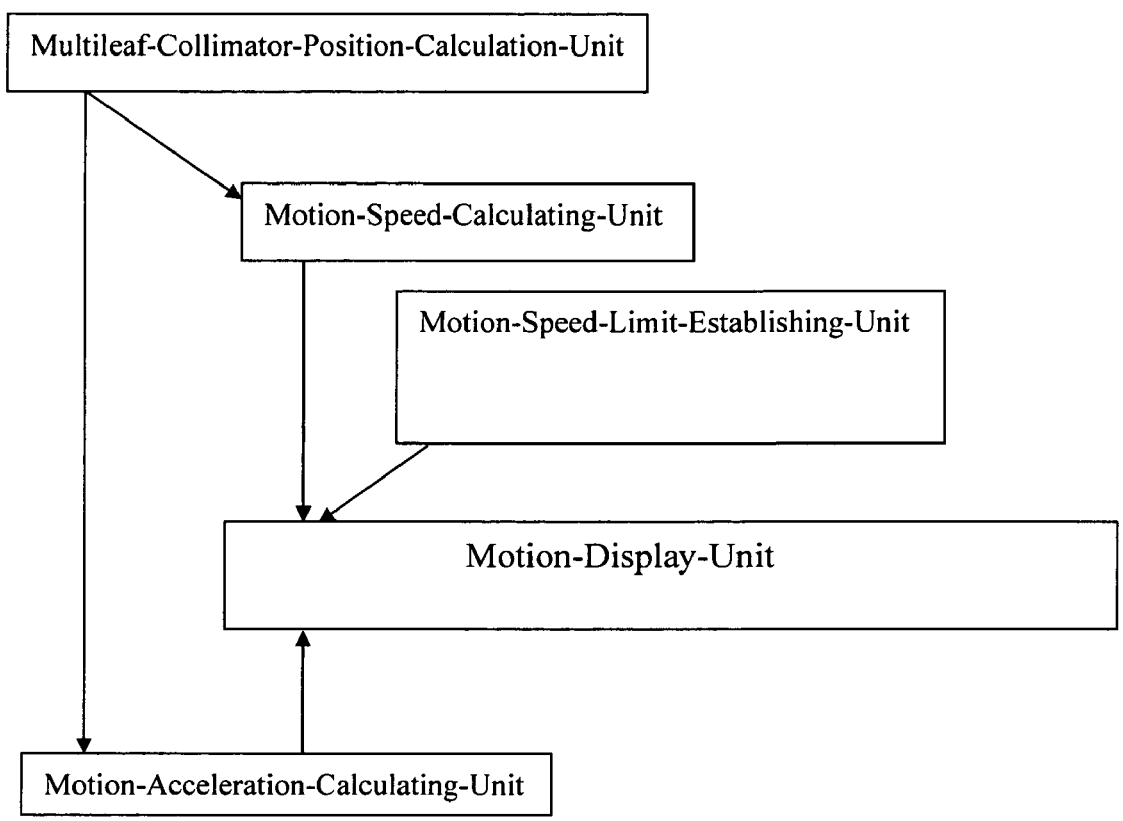
FIG. 14 is a block diagram showing a third aspect of the present invention.
Figure 15:
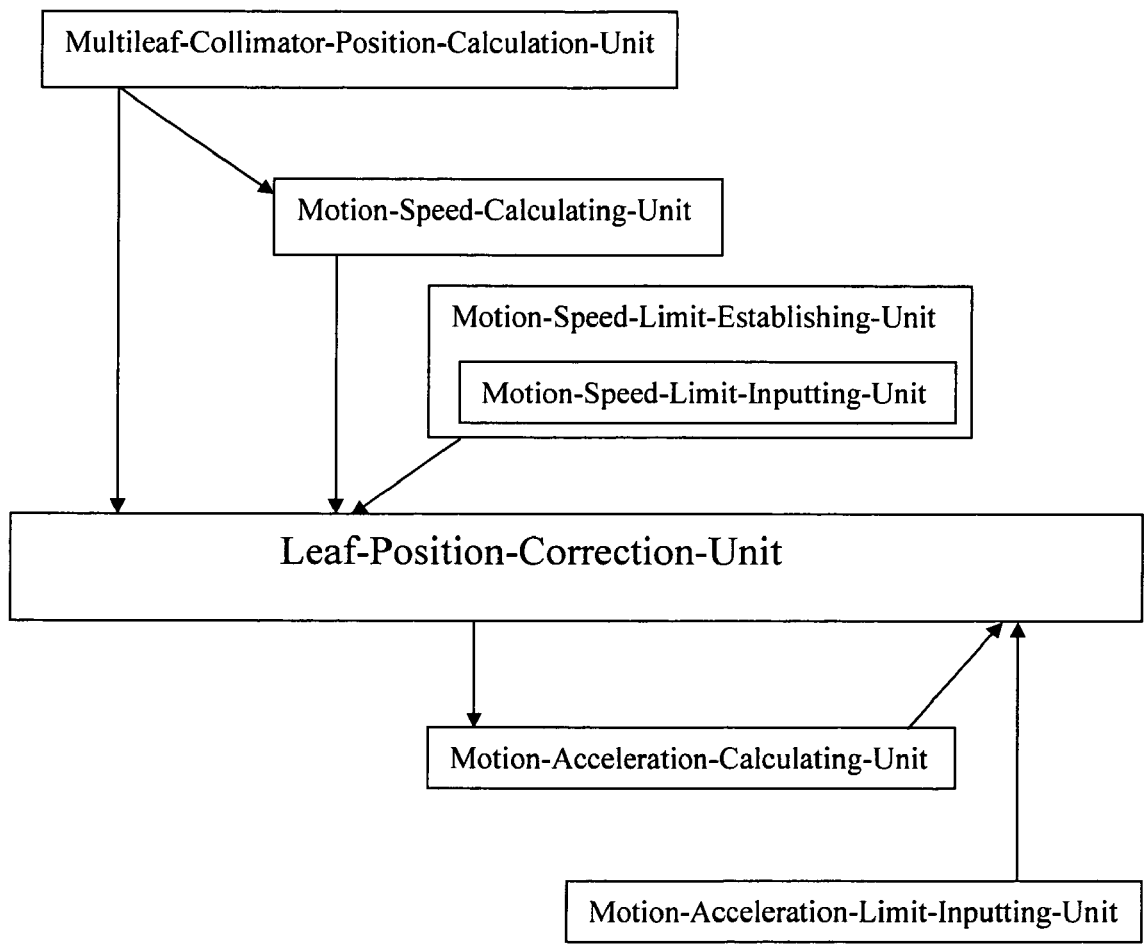
FIG. 15 is a block diagram showing a fourth aspect of the present invention.
Figure 16:
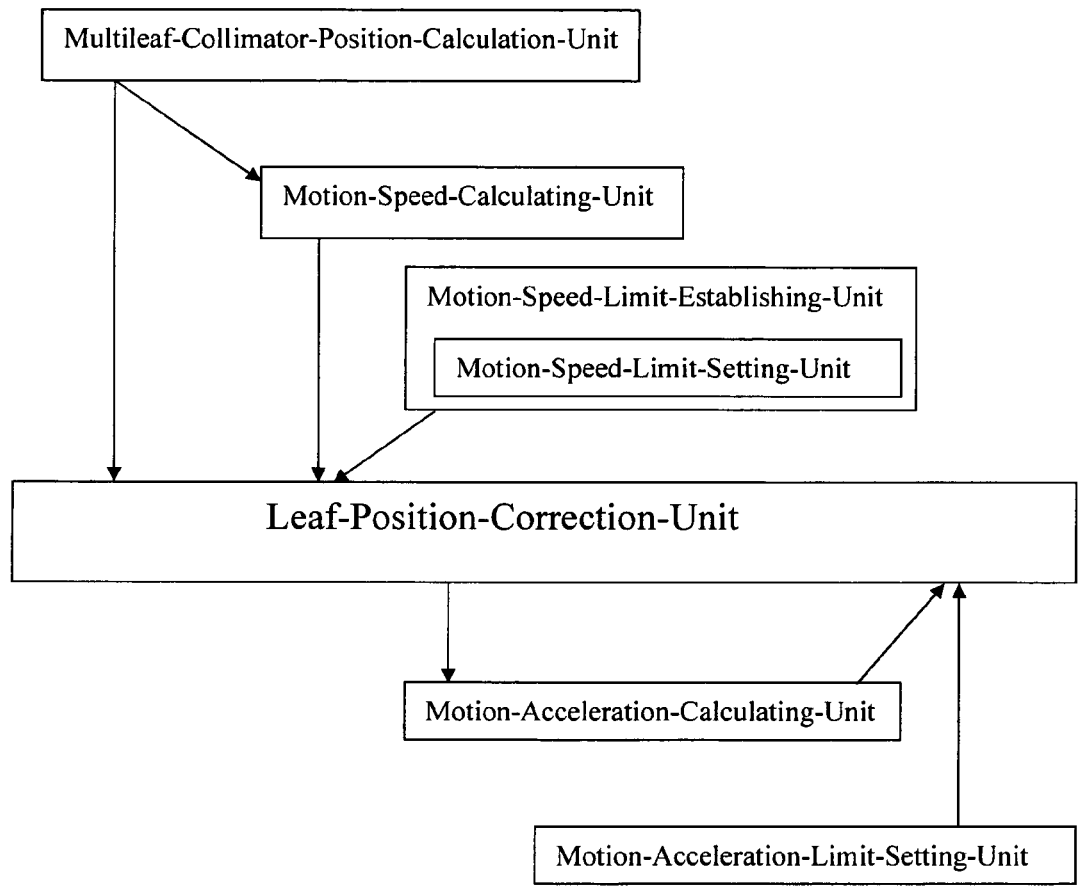
FIG. 16 is a block diagram showing a fifth aspect of the present invention.
Figure 17:
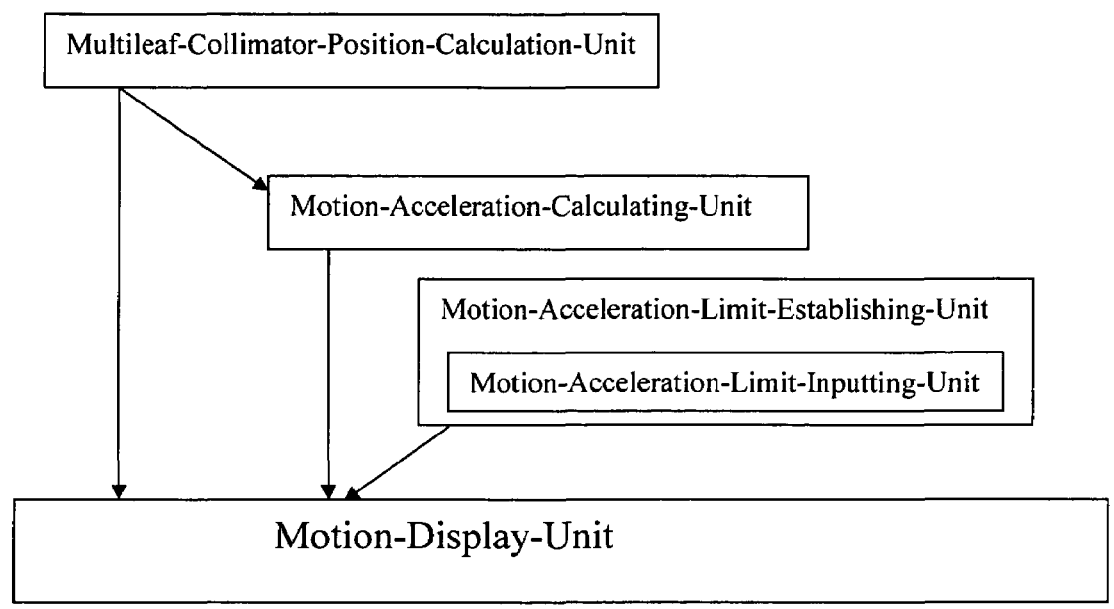
FIG. 17 is a block diagram showing a sixth aspect of the present invention.
Figure 18:
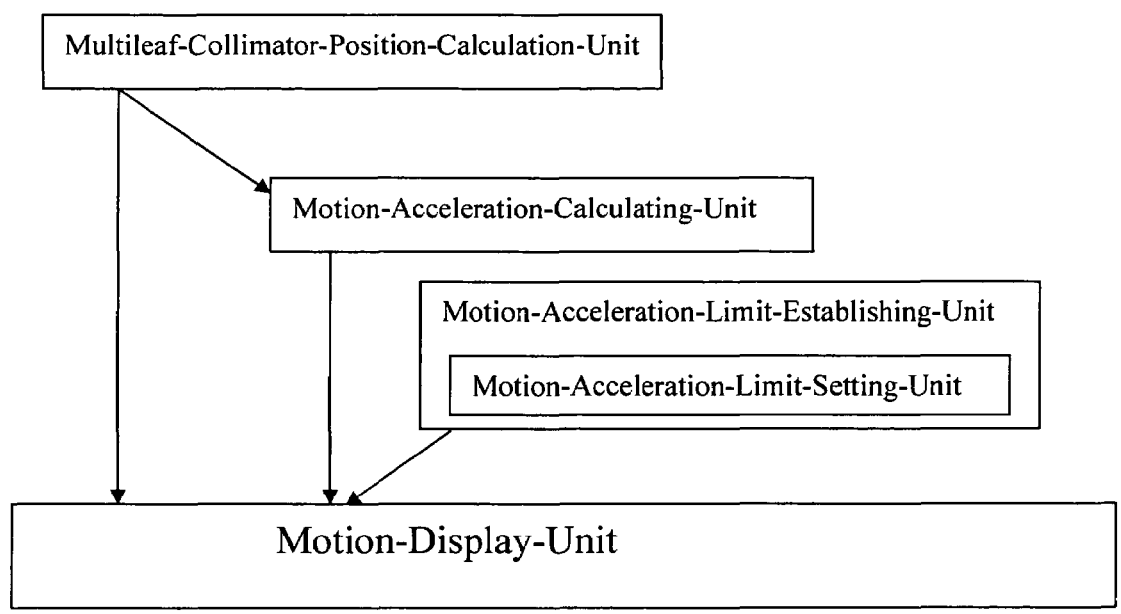
FIG. 18 is a block diagram showing a seventh aspect of the present invention.
Figure 19:
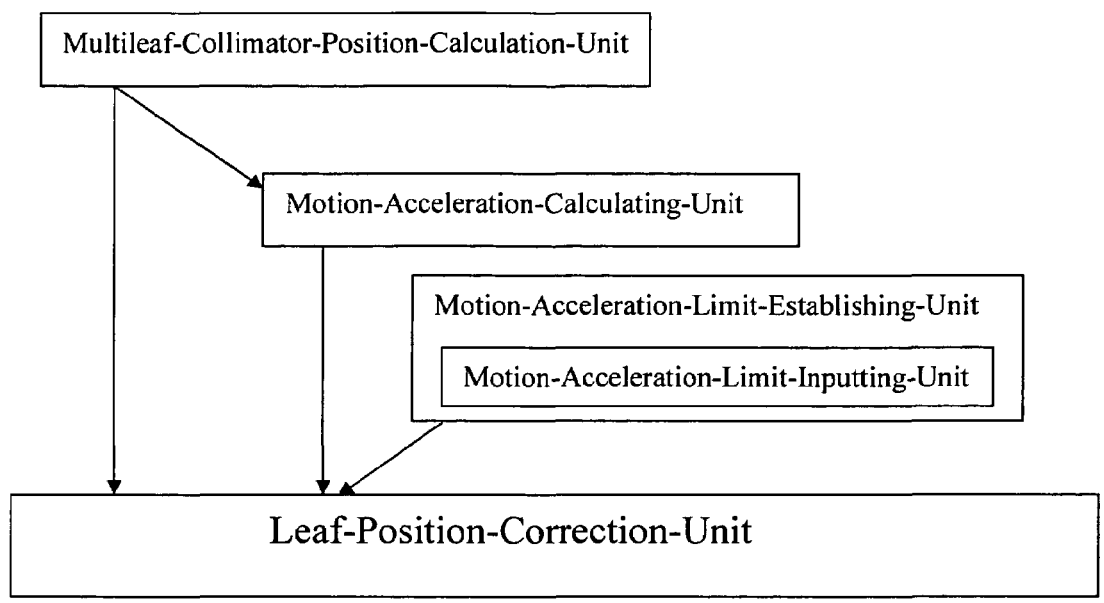
FIG. 19 is a block diagram showing an eighth aspect of the present invention.
Figure 20:
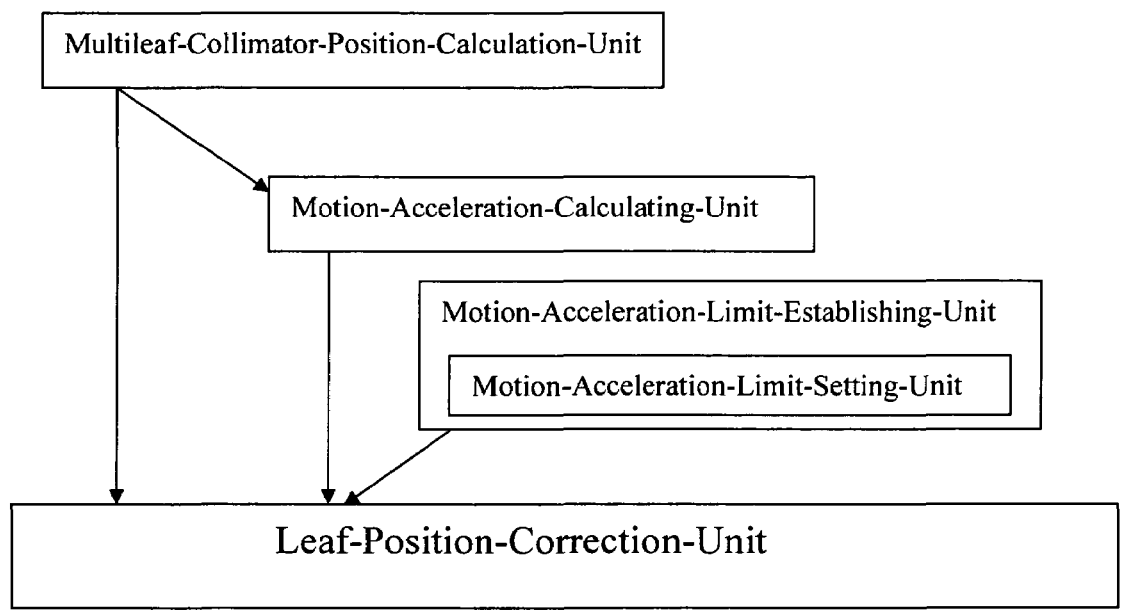
FIG. 20 is a block diagram showing a ninth aspect of the present invention.

FIG. 5 shows motion of a pair of leaves during irradiation with IMRT sliding window method. In the drawing, reference number 51 indicates a curve of a leaf's trace with the sliding window method, reference number 52 indicates a curve of the opposite leaf's trace with the sliding window method, reference (a) is a dotted line of a case which opens the leaf, and reference (b) is a dotted line of a case which closes the leaf. With the sliding window method, the leaves move and the radiation field shape changes during irradiation. Since there is an area where the motion distance exceeds the limit around the center of the drawing, the leaf positions are corrected to the dotted lines (a) and (b) by the Leaf-Position-Correction-Unit. The condition determines which correction would be more preferable, to open or to close.

In place of the Leaf-Position-Correction-Unit of the present embodiment, or along with the Leaf-Position-Correction-Unit, it is possible to comprise a Motion-Display-Unit. The Motion-Display-Unit shows the information of the area where the motion speed (acceleration) calculated by the Motion-Speed(Acceleration)-Calculating-Unit exceeds the speed (acceleration) limit. As an example, the speed (acceleration) which exceeds the limit can be indicated on the display with the gantry angles. Similarly, a chart like FIG. 1 can be displayed (e.g. area 14 where the speed exceeds the limit is a red line, and the other areas are black lines). By using this information to warn the operator, it is possible to adjust the irradiation parameter to avoid a warning arising. As described in the present embodiment, by using the irradiation data for linacs generated by the RTP machine according to the present invention, it is possible to prevent the suspension of treatment due to an MLC positioning error, which exceeds its tolerance, thereby making it possible to improve the efficiency of the radiation therapy and to decrease the patient's discomfort.

What is claimed is:

1. A radiation therapy treatment planning machine for use with a multileaf collimator, said machine comprising:
   a Multileaf-Collimator-Position-Calculation-Unit that generates multileaf collimator leaf positions as a time series;
   a Motion-Speed-Calculating-Unit that calculates leaf motion speed based on the generated time series leaf positions;
   a Motion-Speed-Limit-Establishing-Unit that establishes a motion speed limit of the leaves; and
   a Motion-Display-Unit that indicates leaf motion information and indicates the motion information of an area where the calculated motion speed exceeds the established motion speed limit.

2. The radiation therapy treatment planning machine according to claim 1, wherein said Motion-Speed-Limit-Establishing-Unit comprises a Motion-Speed-Limit-Inputting-Unit that inputs a motion speed limit of the leaves as the established motion speed limit.

3. The radiation therapy treatment planning machine according to claim 2, further comprising:
   a Motion-Acceleration-Calculating-Unit that calculates leaf motion acceleration based on the time series leaf positions generated by said Multileaf-Collimator-Position-Calculation-Unit; and
   a Motion-Acceleration-Limit-Inputting-Unit that inputs a motion acceleration limit of the leaves,
   wherein said Motion-Display-Unit indicates the motion information of an area where the calculated motion acceleration exceeds the inputted acceleration limit.

4. The radiation therapy treatment planning machine according to claim 1, wherein said Motion-Speed-Limit-Establishing-Unit comprises a Motion-Speed-Limit-Setting-Unit that sets a predetermined motion speed limit of the leaves as the established motion speed limit.

5. The radiation therapy treatment planning machine according to claim 4, further comprising:
   a Motion-Acceleration-Calculating-Unit that calculates leaf motion acceleration based on the time series leaf positions generated by said Multileaf-Collimator-Position-Calculation-Unit; and
   a Motion-Acceleration-Limit-Setting-Unit that sets a predetermined motion acceleration limit of the leaves,
   wherein said Motion-Display-Unit indicates the motion information of an area where the calculated motion acceleration exceeds the predetermined set acceleration limit.

6. The radiation therapy treatment planning machine according to claim 1, further comprising:
   a Motion-Acceleration-Calculating-Unit that calculates leaf motion acceleration based on the time series leaf positions generated by said Multileaf-Collimator-Position-Calculation-Unit,
   wherein said Motion-Display-Unit indicates the motion information of an area where the calculated motion acceleration exceeds a motion acceleration limit.

7. A radiation therapy treatment planning machine for use with a multileaf collimator, said machine comprising:
   a Multileaf-Collimator-Position-Calculation-Unit that generates multileaf collimator leaf positions as a time series;
   a Motion-Speed-Calculating-Unit that calculates leaf motion speed based on the generated time series leaf positions;
   a Motion-Speed-Limit-Establishing-Unit that establishes a motion speed limit of the leaves; and
   a Leaf-Position-Correction-Unit that corrects the leaf positions of an area, where the calculated motion speed exceeds the established motion speed limit, such that the leaf motion speed is equal to or less than the established motion speed limit.

8. The radiation therapy treatment planning machine according to claim 7, wherein said Motion-Speed-Limit-Establishing-Unit comprises a Motion-Speed-Limit-Inputting-Unit that inputs a motion speed limit of the leaves as the established motion speed limit.

9. The radiation therapy treatment planning machine according to claim 8, wherein the leaf positions are corrected toward a direction to widen the radiation field shape when said Leaf-Position-Correction-Unit corrects the leaf positions of an area where the calculated motion speed exceeds the inputted motion speed limit such that the leaf motion speed is equal to or less than the inputted motion speed limit.

10. The radiation therapy treatment planning machine according to claim 9, further comprising:
    a Motion-Acceleration-Calculating-Unit that calculates leaf motion acceleration based on the leaf positions corrected by said Leaf-Position-Correction-Unit; and
    a Motion-Acceleration-Limit-Inputting-Unit that inputs a motion acceleration limit of the leaves,
    wherein said Leaf-Position-Correction-Unit corrects the leaf positions of an area, where the calculated motion acceleration exceeds the inputted acceleration limit, such that the leaf motion acceleration is equal to or less than the inputted acceleration limit.

11. The radiation therapy treatment planning machine according to claim 8, wherein the leaf positions are corrected toward a direction to narrow the radiation field shape when said Leaf-Position-Correction-Unit corrects the leaf positions of an area where the calculated motion speed exceeds the inputted motion speed limit such that the leaf motion speed is equal to or less than the inputted motion speed limit.

12. The radiation therapy treatment planning machine according to claim 11, further comprising:
    a Motion-Acceleration-Calculating-Unit that calculates leaf motion acceleration based on the leaf positions corrected by said Leaf-Position-Correction-Unit; and
    a Motion-Acceleration-Limit-Inputting-Unit that inputs a motion acceleration limit of the leaves,
    wherein said Leaf-Position-Correction-Unit corrects the leaf positions of an area, where the calculated motion acceleration exceeds the inputted acceleration limit, such that the leaf motion acceleration is equal to or less than the inputted acceleration limit.

13. The radiation therapy treatment planning machine according to claim 8, further comprising:
    a Motion-Acceleration-Calculating-Unit that calculates leaf motion acceleration based on the leaf positions corrected by said Leaf-Position-Correction-Unit; and
    a Motion-Acceleration-Limit-Inputting-Unit that inputs motion acceleration limit of the leaves,
    wherein said Leaf-Position-Correction-Unit corrects the leaf positions of an area, where the calculated motion acceleration exceeds the inputted acceleration limit, such that the leaf motion acceleration is equal to or less than the inputted acceleration limit.

14. The radiation therapy treatment planning machine according to claim 7, wherein said Motion-Speed-Limit-Establishing-Unit comprises a Motion-Speed-Limit-Setting-Unit that sets a predetermined motion speed limit of the leaves as the established motion speed limit.

15. The radiation therapy treatment planning machine according to claim 14, wherein the leaf positions are corrected toward a direction to widen the radiation field shape when said Leaf-Position-Correction-Unit corrects the leaf positions of an area where the calculated motion speed exceeds the predetermined set motion speed limit such that the leaf motion speed is equal to or less than the predetermined set motion speed limit.

16. The radiation therapy treatment planning machine according to claim 15, further comprising:
 a Motion-Acceleration-Calculating-Unit that calculates leaf motion acceleration based on the leaf positions corrected by said Leaf-Position-Correction-Unit; and
 a Motion-Acceleration-Limit-Setting-Unit that sets a motion acceleration limit of the leaves,
 wherein said Leaf-Position-Correction-Unit corrects the leaf positions of an area, where the calculated motion acceleration exceeds the predetermined set acceleration limit, such that the leaf motion acceleration is equal to or less than the predetermined set acceleration limit.

17. The radiation therapy treatment planning machine according to claim 14, wherein the leaf positions are corrected toward a direction to narrow the radiation field shape when said Leaf-Position-Correction-Unit corrects the leaf positions of an area where the calculated motion speed exceeds the predetermined set motion speed limit such that the leaf motion speed is equal to or less than the predetermined set motion speed limit.

18. The radiation therapy treatment planning machine according to claim 17, further comprising:
 a Motion-Acceleration-Calculating-Unit that calculates leaf motion acceleration based on the leaf positions corrected by said Leaf-Position-Correction-Unit; and
 a Motion-Acceleration-Limit-Setting-Unit that sets a motion acceleration limit of the leaves,
 wherein said Leaf-Position-Correction-Unit corrects the leaf positions of an area, where the calculated motion acceleration exceeds the predetermined set acceleration limit, such that the leaf motion acceleration is equal to or less than the predetermined set acceleration limit.

19. The radiation therapy treatment planning machine according to claim 14, further comprising:
 a Motion-Acceleration-Calculating-Unit that calculates leaf motion acceleration based on the leaf positions corrected by said Leaf-Position-Correction-Unit; and
 a Motion-Acceleration-Limit-Setting-Unit that sets a predetermined motion acceleration limit of the leaves,
 wherein said Leaf-Position-Correction-Unit corrects the leaf positions of an area, where the calculated motion acceleration exceeds the predetermined set acceleration limit, such that the leaf motion acceleration is equal to or less than the predetermined set acceleration limit.

20. A radiation therapy treatment planning machine for use with a multileaf collimator, said machine comprising:
 a Multileaf-Collimator-Position-Calculation-Unit that generates multileaf collimator leaf positions as a time series;
 a Motion-Acceleration-Calculating-Unit that calculates leaf motion acceleration based on the generated time series leaf positions;
 a Motion-Acceleration-Limit-Establishing-Unit that establishes a motion acceleration limit of the leaves; and
 a Motion-Display-Unit that indicates leaf motion information of an area where the calculated motion acceleration exceeds the established acceleration limit.

21. The radiation therapy treatment planning machine according to claim 20, wherein said Motion-Acceleration-Limit-Establishing-Unit comprises a Motion-Acceleration-Limit-Inputting-Unit that inputs a motion acceleration limit of the leaves as the established motion acceleration limit.

22. The radiation therapy treatment planning machine according to claim 20, wherein said Motion-Acceleration-Limit-Establishing-Unit comprises a Motion-Acceleration-Limit-Setting-Unit that sets a predetermined motion acceleration limit of the leaves as the established motion acceleration limit.

23. A radiation therapy treatment planning machine for use with a multileaf collimator, said machine comprising:
 a Multileaf-Collimator-Position-Calculation-Unit that generates multileaf collimator leaf positions as a time series;
 a Motion-Acceleration-Calculating-Unit that calculates leaf motion acceleration based on the generated time series leaf positions;
 a Motion-Acceleration-Limit-Establishing-Unit that establishes a motion acceleration limit of the leaves; and
 a Leaf-Position-Correction-Unit that corrects the leaf positions of an area, where the calculated motion acceleration exceeds the established motion acceleration limit, such that the leaf motion acceleration is equal to or less than the established motion acceleration limit.

24. The radiation therapy treatment planning machine according to claim 23, wherein said Motion-Acceleration-Limit-Establishing-Unit comprises a Motion-Acceleration-Limit-Inputting-Unit that inputs a motion acceleration limit of the leaves as the established motion acceleration limit.

25. The radiation therapy treatment planning machine according to claim 23, wherein said Motion-Acceleration-Limit-Establishing-Unit comprises a Motion-Acceleration-Limit-Setting-Unit that sets a predetermined motion acceleration limit of the leaves as the established motion acceleration limit.

\* \* \* \* \*